US010268229B2

(12) United States Patent
Stever

(10) Patent No.: US 10,268,229 B2
(45) Date of Patent: Apr. 23, 2019

(54) ADJUSTABLE ELECTRICAL EQUIPMENT

(71) Applicant: ZOLL Medical Corporation, Chelmsford, MA (US)

(72) Inventor: Timothy F. Stever, Lowell, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 253 days.

(21) Appl. No.: 14/978,396

(22) Filed: Dec. 22, 2015

(65) Prior Publication Data

US 2016/0179126 A1 Jun. 23, 2016

Related U.S. Application Data

(60) Provisional application No. 62/096,298, filed on Dec. 23, 2014.

(51) Int. Cl.
| | |
|---|---|
| *G05F 5/00* | (2006.01) |
| *H02J 7/00* | (2006.01) |
| *A61N 1/39* | (2006.01) |
| *B06B 1/02* | (2006.01) |

(52) U.S. Cl.
CPC ............. *G05F 5/00* (2013.01); *H02J 7/0063* (2013.01); *A61N 1/3975* (2013.01); *B06B 1/0246* (2013.01); *H02J 2007/0067* (2013.01)

(58) Field of Classification Search
CPC ...... A61N 1/3975; A61N 1/3925; A61N 1/39; A61N 1/3904; A61N 1/3937; A61N 1/3981; A61N 1/00734; B06B 1/0246
USPC ...................................................... 307/24, 51
See application file for complete search history.

(56) References Cited

U.S. PATENT DOCUMENTS

| | | | |
|---|---|---|---|
| 4,839,248 A | 6/1989 | Magnussen, Jr. et al. | |
| 5,800,460 A | 9/1998 | Powers et al. | |
| 5,869,970 A * | 2/1999 | Palm | A61N 1/3708 324/433 |
| 5,879,374 A | 3/1999 | Powers et al. | |
| 6,118,251 A | 9/2000 | Atwater | |
| 6,261,249 B1 * | 7/2001 | Talish | A61B 8/4227 600/459 |
| 6,826,427 B1 * | 11/2004 | Fayram | A61N 1/3975 607/29 |
| 7,009,363 B2 | 3/2006 | Beals et al. | |
| 8,456,134 B2 | 6/2013 | Gajewski | |
| 9,393,433 B2 * | 7/2016 | Parramon | A61N 1/08 |
| 9,526,920 B2 * | 12/2016 | Tanis | A61N 7/00 |
| 2003/0040775 A1 | 2/2003 | Faller et al. | |
| 2005/0177198 A1 * | 8/2005 | Norton | A61N 1/378 607/29 |
| 2006/0022645 A1 * | 2/2006 | Bowers | H02J 7/0047 320/132 |

(Continued)

*Primary Examiner* — Adam D Houston
(74) *Attorney, Agent, or Firm* — ZOLL Medical Corporation

(57) ABSTRACT

An electrical apparatus includes a battery and an adjustable circuit. The adjustable circuit is configured to adjust a load current in the electrical equipment when battery impedance for the battery is higher than a predetermined threshold battery impedance. The battery impedance for the battery is compared in a session against the predetermined threshold battery impedance and the load current is adjusted in the session when the predetermined threshold battery impedance is higher than the predetermined threshold battery impedance.

26 Claims, 8 Drawing Sheets

(56) References Cited

U.S. PATENT DOCUMENTS

| | | | |
|---|---|---|---|
| 2011/0316484 A1* | 12/2011 | de Wit | H01M 4/382 |
| | | | 320/135 |
| 2012/0112690 A1* | 5/2012 | Stulen | A61B 17/00234 |
| | | | 320/108 |
| 2016/0179126 A1* | 6/2016 | Stever | G05F 5/00 |
| | | | 307/24 |
| 2016/0274162 A1* | 9/2016 | Freeman | A61H 3/00 |
| 2017/0188979 A1* | 7/2017 | Volpe | A61B 5/7282 |
| 2017/0271648 A1* | 9/2017 | Zaghib | H01G 11/42 |

* cited by examiner

ADJUSTABLE ELECTRICAL EQUIPMENT

CROSS REFERENCE TO RELATED APPLICATION

The present application claims the benefit of U.S. Provisional Application No. 62/096,298 filed on Dec. 23, 2014. The entire disclosure of the above-identified application is expressly incorporated by reference herein in its entirety.

BACKGROUND

1. Field of the Disclosure

The present disclosure relates to the field of electrical equipment. More particularly, the present disclosure relates to adjusting electrical equipment.

2. Background Information

A battery consists of at least two cells connected in series. Cells have a positive end and a negative end, so when the cells are connected end to end, the resulting battery also has a positive end and a negative end. An electrode on one end of a cell or battery is a cathode and an electrode on the other end is an anode. The cathode and anode are oppositely positive or negative (i.e., polar), and the polarity of each depends on whether a cell or battery is charging or discharging.

Passivation of either or both of the cell or battery electrodes can affect the performance of the cell or battery. Passivation is a term used to describe reduced chemical reactivity of a surface such as a surface of an electrode. For an electrical device, apparent internal battery impedance for a battery in the device can grow over time for reasons including, but not limited to, battery electrode passivation. Passivation can increase both with time and with temperature. A passivation layer typically has high impedance, which can cause a lowered voltage of the cell or battery when a load is applied during use.

DETAILED DESCRIPTION

In view of the foregoing, the present disclosure, through one or more of its various aspects, embodiments and/or specific features or sub-components, is thus intended to bring out one or more of the advantages as specifically noted below.

Methods described herein are illustrative examples, and as such are not intended to require or imply that any particular process of any embodiment be performed in the order presented. Words such as "thereafter," "then," "next," etc. are not intended to limit the order of the processes, and these words are instead used to guide the reader through the description of the methods. Further, any reference to claim elements in the singular, for example, using the articles "a," "an" or "the", is not to be construed as limiting the element to the singular.

As described herein, when an electrical device is started, apparent internal battery impedance of a battery can be measured. The measurement can be when the electrical device is started for normal operation, when the electrical device is periodically tested such as in a periodic test, or when the electrical device is dynamically tested such as by a test performed specifically in response to receipt of an instruction or control operation. The apparent internal battery impedance can be measured by measuring the current and battery output voltage with two different loads applied. The two different loads (i.e., impedance of the loads) do not have to be measured as the values of the different loads are not required for the processes described herein. The test may be a self-test or alternatively a test administered in whole or in part by a connected unit or even in part over a network by a remote testing unit.

As described herein, battery impedance due to passivation can be reduced by increasing a load current so as to "burn off" the extra battery impedance due to passivation. The increased load current can be dynamically implemented in response to measurement and confirmation of the extra battery impedance. The load current can also be dynamically adjusted from a low to high value or a high to low value based on the measured magnitude of the extra impedance or the resilience of the passivation in the face of load currents already applied. Measurements can be repeatedly obtained until the apparent internal battery impedance drops to an acceptable level such as to or below a preset threshold.

Figure 1:
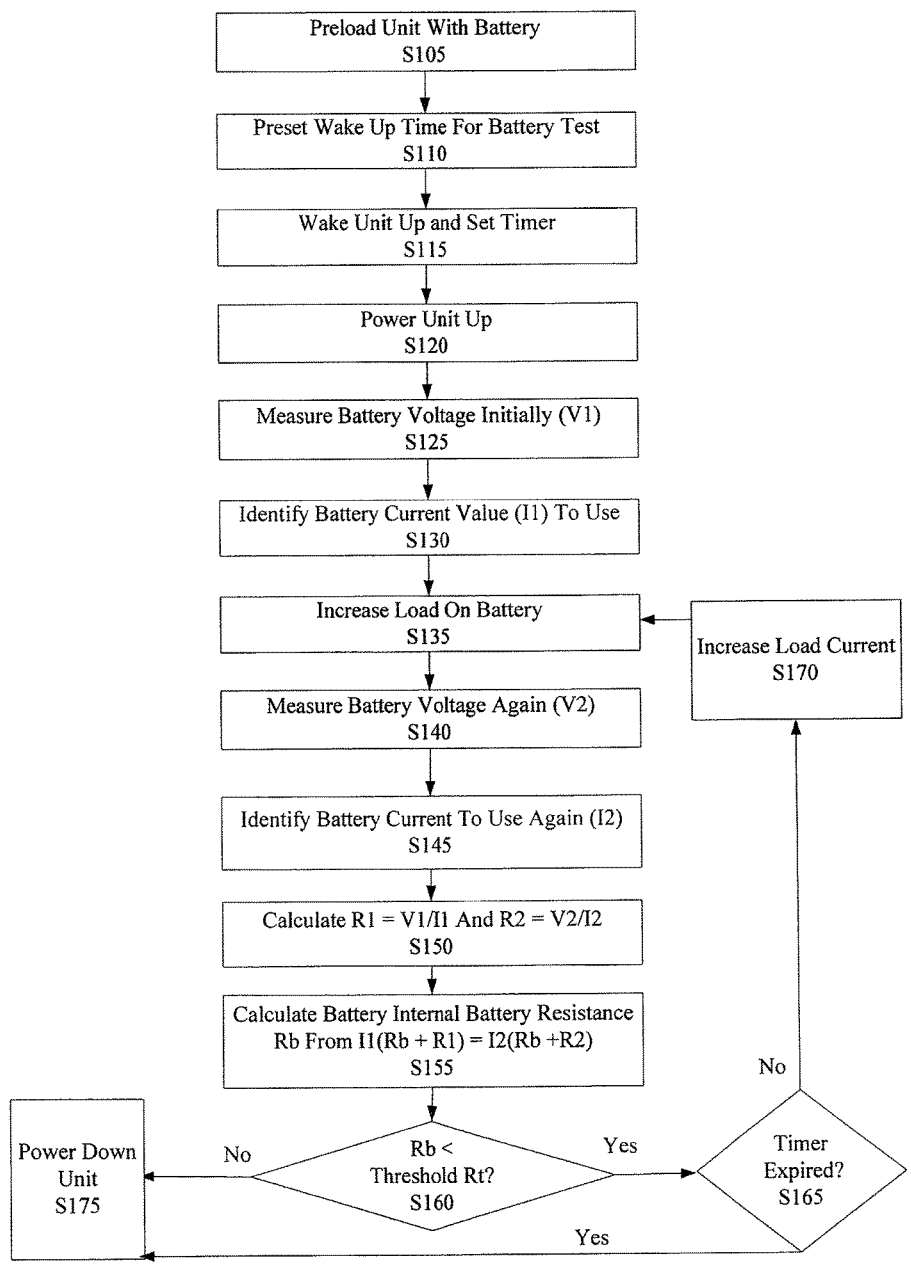
FIG. 1 shows an exemplary method for adjustable electrical equipment, according to an aspect of the present disclosure.

FIG. 1 shows an exemplary method for adjustable electrical equipment, according to an aspect of the present disclosure. In FIG. 1, a unit is preloaded with a battery at S105. A unit as described herein is a piece of electrical equipment, such as a defibrillator. The unit may be self-contained, such as a wall-mounted unit that is only occasionally used. The unit may be provided without a capability to communicate externally such as with a hardwired proximate controller or over a wireless network with a centralized remote controller. Thus, the battery may be preloaded when the electrical equipment is built at a factory, when the electrical equipment is installed for use, or anywhere in between.

At S110, the unit is preset with a wake-up time to conduct a battery test. The wake-up time can be non-periodic, such as on the 15$^{th}$ of every month, on the second Saturday of every month, or even on multiple alternating or overlapping schedules. Alternatively, the wake-up time may be programmed to be periodic, such as daily, weekly, monthly, quarterly, or yearly. The wake-up time may be specifically set as a time when the unit is unlikely to be in use, such as in the early morning. The preset wake-up time may be stored as an instruction in a memory, or used as a clock setting for a clock provided with the electrical equipment.

As an alternative to the wake-up time preset at S110, the unit may be dynamically instructed by a controller when to conduct a battery test. As another alternative, however, the battery test may be conducted when the electrical equipment is opened or started for its intended purpose. In other words, the battery test may be performed based on detection of a specific action, even when performance of the battery test is not the primary reason the specific action is being taken.

A session as described herein is marked between a starting point and an ending point. Testing and adjustment as described herein may be limited to a single session, such that if the session is interrupted the testing and adjustment are stopped. The session may be defined as a period between a starting point and an ending point that is not interrupted by another starting point and/or ending point. The starting point may be when a unit is turned on and the ending point may be when the unit is turned off. The starting point may be when a unit is woken up and the ending point may be when the unit is put back to sleep. The starting point may be when a start signal is received, such as when a button is pushed or a start is otherwise physically detected, and the ending point may be when the button is again pushed or when the end is otherwise physically detected. The starting point may be when a signal is received and the ending point may be when another signal is received or a clock/timer expires. The starting point may be when a clock is preset to start and the ending point may be after a predetermined amount of time passes after the preset starting point. The ending point may alternatively be independent of the passage of time, such as after a predetermined sequence of steps has been completed. That is, the starting point can be a wake up alarm, and the ending point can be when the unit finishes whatever is done in response to the wake up alarm.

A session as described herein may also include continuous activity. The continuous activity may include a series of individual processes or functions, even when a gap exists between individual processes and functions taking place. Individual processes described herein can include, for example:
- a unit turning on and/or just waking up
- checking a clock and marking a start time
- measuring battery resistance or impedance
- comparing measured battery resistance or impedance against a predetermined threshold battery resistance or impedance
- adjusting a load current on a battery
- checking a clock and marking an end time or interim end time
- comparing a duration of start time to end time or interim end time against a preset amount of time
- repeating the turning on/waking up, comparing and adjusting until the end time or preset amount of time is reached A threshold battery resistance may vary, such as based on the age of the battery. That is, a threshold battery resistance may be preset to vary with time so that the threshold used for comparison with a measured value changes as the battery ages. A varying threshold may vary with reference to time measured by a clock that is either internal to the unit or external to the unit.

At S115, the unit is awakened and a timer is set. The unit can be awakened here at the time preset at S110, and this time may be periodic as described above. For example, a unit may be preset to wake up and conduct a test every Monday morning at 2:00 AM, or the first Monday of every month at 2:00 AM. The timer is set so as to set limit the amount of time spent testing and dynamically adjusting the electrical equipment in the manner described herein. Of course, use of a timer is not a requirement for the dynamic adjusting. Limits on the testing and dynamic adjusting can be imposed in other ways such as by limiting the number of iterations that testing and dynamic adjusting is performed.

In the case of medical equipment, the timer may be set at S115 to a very short amount of time, in the order of seconds, to ensure that the dynamic adjustment does not interfere with use of the medical equipment for its intended purpose. This short amount of time may be set when the unit is woken based on a specific act. For example, the amount of time may be set when a casing for the unit is opened. The short amount of time may also be set for any time the testing and dynamic adjustment is to be performed, so as to ensure that the testing and dynamic adjustment do not continue even when the battery resistance is elevated but no further progress is likely in removing a passivation layer.

At S120, the unit is powered up. Of course, the waking at S115 and the powering up at S120 may be performed as a single action. The unit may be fully powered up as much as when the unit is started for normal use, or the powering up may be limited to the battery testing and adjustment described herein such as when the unit is only periodically awakened for the battery testing and adjustment. The settings such as the use and setting of the timer at S115 may vary depending on a previous determination whether the unit is being powered up for its intended use, or only based on an instruction to perform the battery testing and adjustment. The determination whether the unit is being powered up for an intended use or based on a specific instruction to perform the battery testing and adjustment may be performed before S115, such as when an instruction to perform battery testing and adjustment is input, received or otherwise detected and executed.

At S125, the initial battery voltage (V1) is measured. At S130, the initial battery current (I1) to use for the testing and adjustment is identified. The initial battery current (I1) may be identified as an assumed nominal value, or may be actively measured. At S135, the load placed on the battery is increased. A second battery voltage (V2) is measured again at S140 after the load on the battery is increased at S135. At S145, the second battery current (I2) to use for the testing and adjustment is identified.

At S150, an initial load resistance (R1) is calculated by dividing the initial battery voltage (V1) calculated at S125 by the initial battery current (I1) identified at S130. At S150, a second load resistance (R2) is calculated by dividing the second battery voltage (V2) identified at S140 by the second battery current (I2).

At S155, the battery internal resistance (Rb) is calculated by solving for Rb in the equation I1(Rb+R1)=I2(Rb+R2). More precisely, at S155 the battery internal resistance (Rb) is solved as (I2·R2−I1·R1)/(I1−I2) or (I1·R1−I2·R2)/(I2−I1).

At S160, the battery internal resistance (Rb) is compared to a threshold resistance (Rt). If the internal resistance is not above the threshold resistance (Rt) at S160 (S160=No), i.e., the internal resistance (Rb) is equal to or less than the threshold resistance (Rt), than the unit is powered down at S175. The unit can be powered down because the internal resistance (Rb) is below the threshold resistance, such that, for example, passivation would not be expected to cause a significant problem when the electrical equipment is used as intended. If the internal resistance is above the threshold resistance (Rt) at S160 (S160=Yes), then the timer is checked at S165, and if not yet expired (S165=No) the load current is increased at S170. If the timer is expired at S165 (S165=Yes), i.e., the test and adjustment has lasted too long, then the unit is powered down at S175. The increase in load at S170 may be the initial increase from a zero value to a positive value, such as during the first iteration of an iterative process for eliminating passivation. Additionally, load current may be alternatively or additionally decreased in the process of FIG. 1, such as when only a relatively small amount of extra battery resistance remains after most of a passivation layer is eliminated.

The threshold battery internal resistance Rt may be predetermined, such as at a factory that manufactures the battery, or at a distributor that distributes the battery, or at an assembler that assembles the electrical equipment that includes the battery. The threshold battery internal resistance Rt may also change over time, such as by being incrementally raised to allow for normal aging effects of the battery other than passivation. The threshold battery internal resistance Rt may also be instructed in a dynamic instruction by an external controller If the load current is increased at S170, the process starts again at S135 as the load on the battery is increased. Once the process starts again after S170 the first time, the process of testing and adjustment can be considered iterative. The process from S135 to S170 can be repeated several or even many times, depending on context. When the electrical equipment is being tested and adjusted for immediate use, the testing and adjustment may only be repeated once or for very few iterations. For example, when the electrical equipment is being tested and adjusted for immediate use, the testing and adjustment may be limited to a period of 2 seconds. When the electrical equipment is being tested periodically, and is not activated for immediate use however, the testing and adjustment of FIG. 1 can be repeated many times in a longer period, such as 60 or 90 seconds.

In the process of FIG. 1, the internal battery resistance Rb is measured. However, resistance (R) is used instead of impedance (Z) as a matter of expedience for simplicity, such as with a direct current (DC) circuit. For a direct current (DC) circuit, impedance (Z) is the same as resistance (R). In an alternating current (AC) circuit, the load on the battery can be increased at S135 using conductors and/or capacitors or flywheels, such as by charging a parallel capacitor in an open circuit condition with the battery and then applying current from the capacitor to the battery. One or more capacitors can be provided in a switched circuit with variable output current so as to contribute all or part of the load current on the battery at S135. Alternatively, inductors or flywheels can be provided in a switched circuit with variable output current. As described herein, the load on the battery can be increased in order to "burn off" the passivation layer on an electrode of the battery, and the ability to automatically vary the load on a battery can be implemented with many different circuit arrangements using capacitors and/or inductors.

Figure 2:
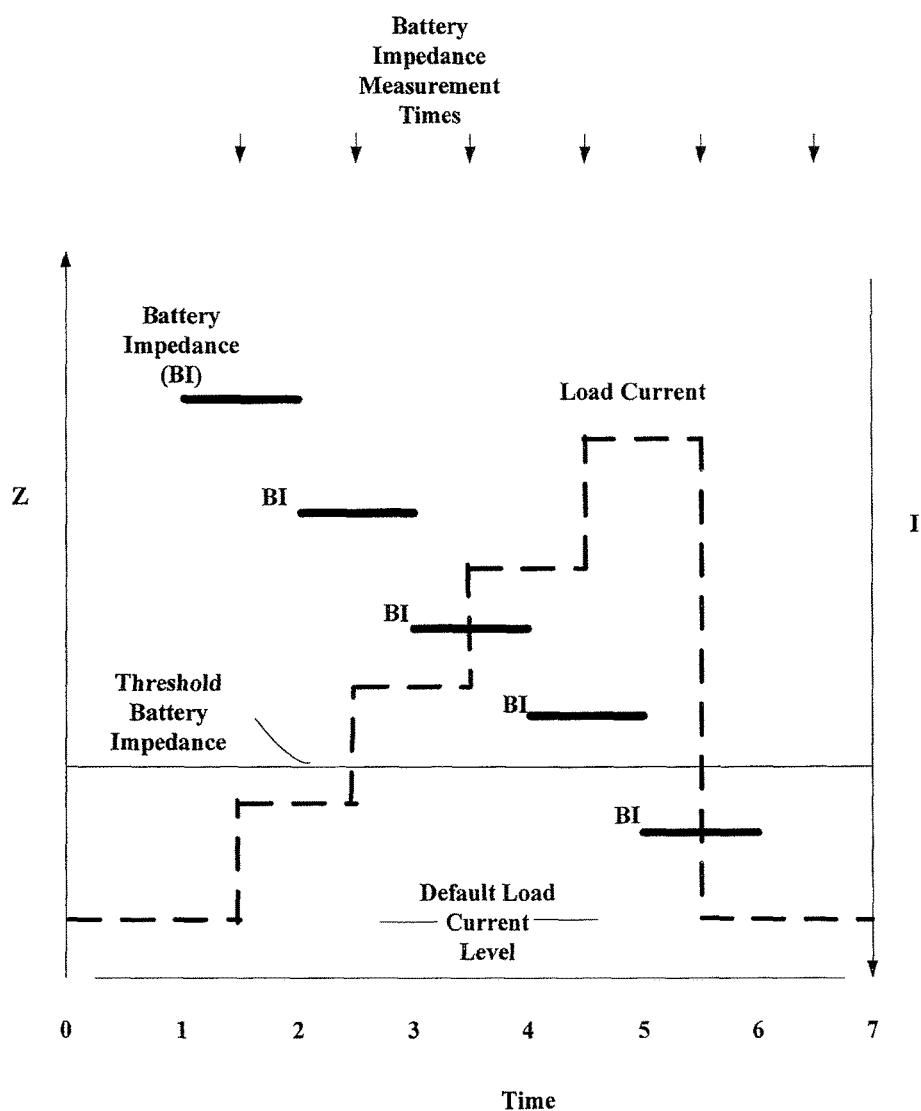
FIG. 2 shows an exemplary timing chart of measured impedance versus load current for adjustable electrical equipment, according to an aspect of the present disclosure.

FIG. 2 shows an exemplary timing chart of measured impedance versus load current for adjustable electrical equipment, according to an aspect of the present disclosure. In FIG. 2, the vertical axis on the left side of the timing chart corresponds to measured impedance Z and the vertical axis on the right side of the timing chart corresponds to load current I. The bottom horizontal axis represents time, and arrows disposed horizontally at the top of FIG. 2 show battery impedance measurement times. In FIG. 2, battery impedance is shown to be a high value at the beginning of the process, but drops below a threshold battery impedance as the load current is increased stepwise. The battery impedance measurement times correspond to increases (starting between times 1 and 2) and decreases (between times 5 and 6) in the load current as the load current is increased to "burn off" passivation, and then reduced back to a default load current level once the battery impedance is measured below the threshold battery impedance.

The battery impedance measured for FIG. 2 may be measured in accordance with the process of FIG. 1, and specifically the process from S125 to S155. However, this is representative of a process for obtaining only battery resistance. Impedance Z is measured by $Z_R+ZL+Z_C$, i.e., and may be obtained by a more complicated calculation. Overall impedance is more specifically represented by the equation $R+j\omega L+1/j\omega C$ where j is the imaginary unit, L is inductance, C is capacitance and $\omega$ is frequency.

In FIG. 2, the beginning and end of the chart may correspond to the beginning and end of a session in which the testing and adjusting are performed. The beginning may be at a preset time, may be based upon an external instruction, or may be based upon a detected act such as the opening of a casing that includes a piece of electrical equipment or the electrical equipment being turned on. The end may be once the load current is back at the default level for a full measurement cycle of, e.g., two consecutive measurement times, or once the measured battery impedance is below the threshold for a full measurement cycle of, e.g., two consecutive measurement times. The end may also be once a timer expires, such as if the timer is set to expire specifically at time "7" no matter the level of the measured battery impedance or the load current. The timer might be selectively used only in specific circumstances and not all circumstances, such as when a piece of medical equipment is opened or started for its intended purpose.

Figure 3:
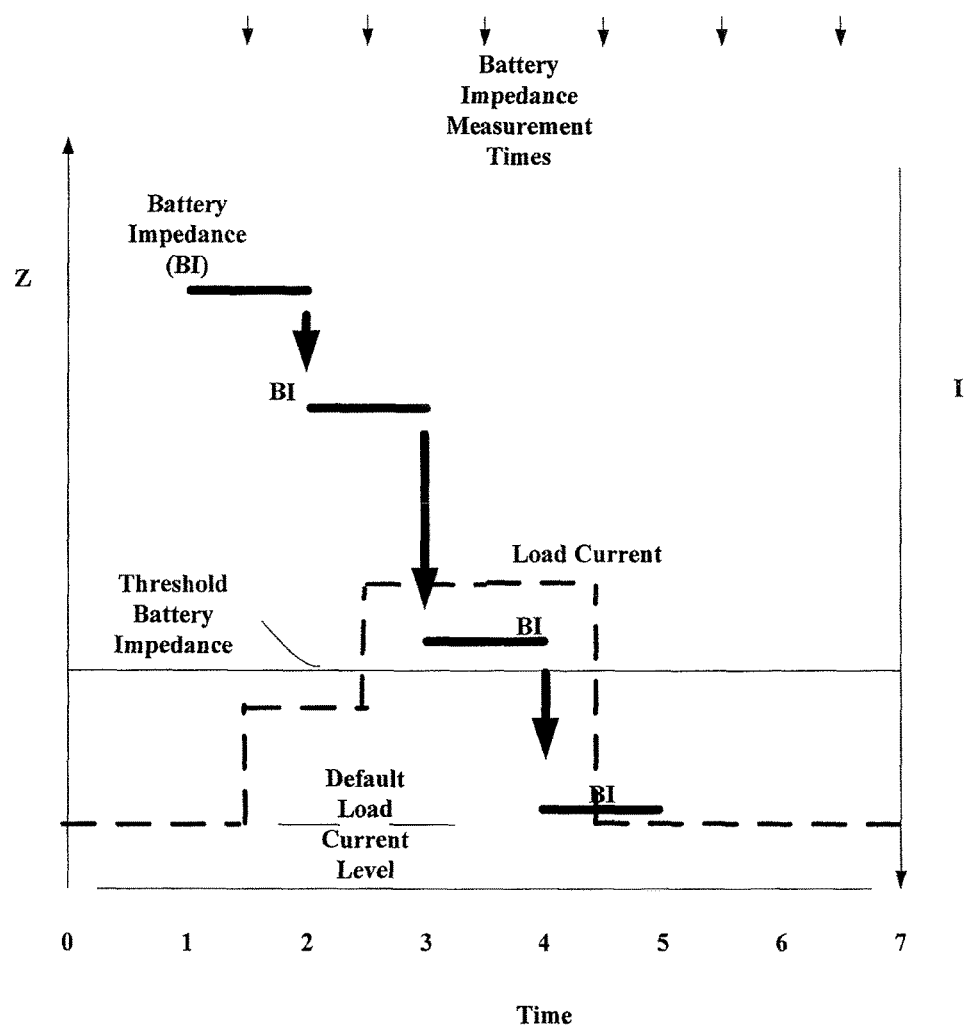
FIG. 3 shows another exemplary timing chart of measured impedance versus load current for adjustable electrical equipment, according to an aspect of the present disclosure.

FIG. 3 shows another exemplary timing chart of measured impedance versus load current for adjustable electrical equipment, according to an aspect of the present disclosure. FIG. 3 is similar to the timing chart of FIG. 2, but shows a cumulative drop in battery impedance based on increases in load current, rather than a stepwise one-to-one correspondence in FIG. 2. FIG. 3 thus represents that drops in internal battery impedance may grow larger between measurements as the load current increases, such that load current may be stepwise increased only a few times, such as one, two or three times, before the passivation layer is fully "burned off". In FIG. 3, the load current can drop to the default load current level between times 4 and 5, and therefore quicker than in FIG. 2. Similarly, the battery impedance drops below the threshold battery impedance at time 4, and therefore quicker than in FIG. 2. Of course, the step-like decreases in impedance are representative of only measured impedance, as the actual impedance is more accurately represented in a continuous decreasing curve in both FIGS. 2 and 3 as the load current is applied.

In both FIGS. 2 and 3, the load current is applied if the measured battery impedance is above a threshold. However, if an initial measurement of battery impedance is not above the threshold battery impedance, than the load current need not be applied at all. Similarly, the load current once applied is shown to be dropped back to a default level once the measured battery impedance is below the threshold battery impedance. However, in a switched variable circuit, the load current may be entirely discontinued once the process of testing and adjustment described herein is concluded. The load current may be a single-use current that is only used for reducing passivation, and the source of the load current may otherwise not be used such as when the electrical equipment is used for its intended purpose. A special-purpose variable circuit as described herein may be used, such as for electrical equipment that is rarely used. A special-purpose variable circuit may also be used for electrical equipment that is likely to be in disuse for a lengthy period, such that passivation is likely to increase the battery impedance beyond a tolerable level.

Figure 4:
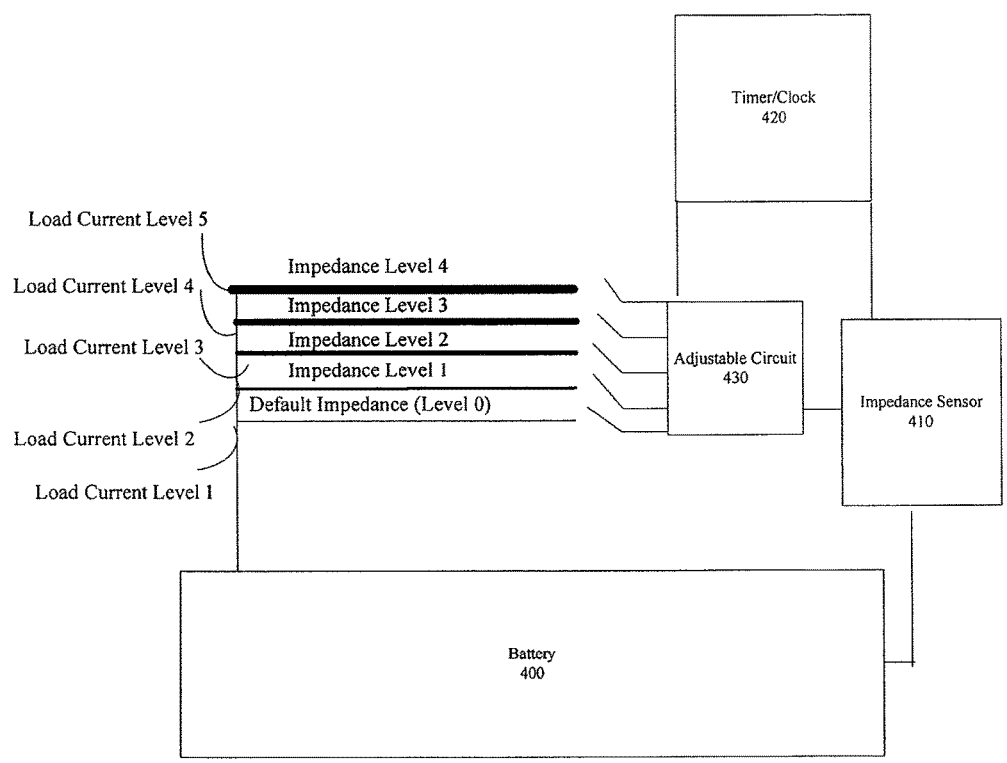
FIG. 4 shows an exemplary piece of adjustable electrical equipment, according to an aspect of the present disclosure.

FIG. 4 shows an exemplary piece of adjustable electrical equipment, according to an aspect of the present disclosure. In FIG. 4, an impedance sensor 410 senses internal impedance of a battery 400, and an adjustable circuit 430 includes one or more switches that can switch elements used to change the load current based on the sensed impedance. As noted throughout this disclosure, the load current is increased in order to "burn off" the passivation. The load current may be varied between two levels such as 0 and 1, or may be varied between multiple levels that result from active selections of elements such as one or more resistors (or other elements that impose a load) in the adjustable circuit 430. In an embodiment, the load current may also be provided from a source other than the battery 400, such as a secondary battery or other additional power source dedicated or otherwise used to provide a load current for eliminating passivation on a primary battery 400.

The embodiment of FIG. 4 shows a mechanism for switching between load current levels responsive to identification/measurement of different impedance levels. This selection/switching mechanism of the adjustable circuit 430 can correspond to switching between multiple resistors (or other elements that impose a load), or to variations in the amount and length of time a single capacitor is charged. Another way to apply a load to a battery with an adjustable circuit 430 is to drive a constant current circuit with an adjustable control signal. A constant current circuit can be a transistor-based circuit used to apply a load to a battery. As noted herein, other circuit elements can also be used in order to increase the load on a battery.

In FIG. 4, a timer 420 is also provided, so as to limit the amount of time testing and adjustment is performed. The timer 420 may be used selectively, such as when the electrical equipment that includes battery 400 is opened or started for its intended use. Alternatively, the timer 420 may be used always, such as when a particular amount of time or high internal impedance readings is deemed enough to consistently and always judge that the battery impedance cannot be effectively reduced by application of an increased load current.

Figure 5:
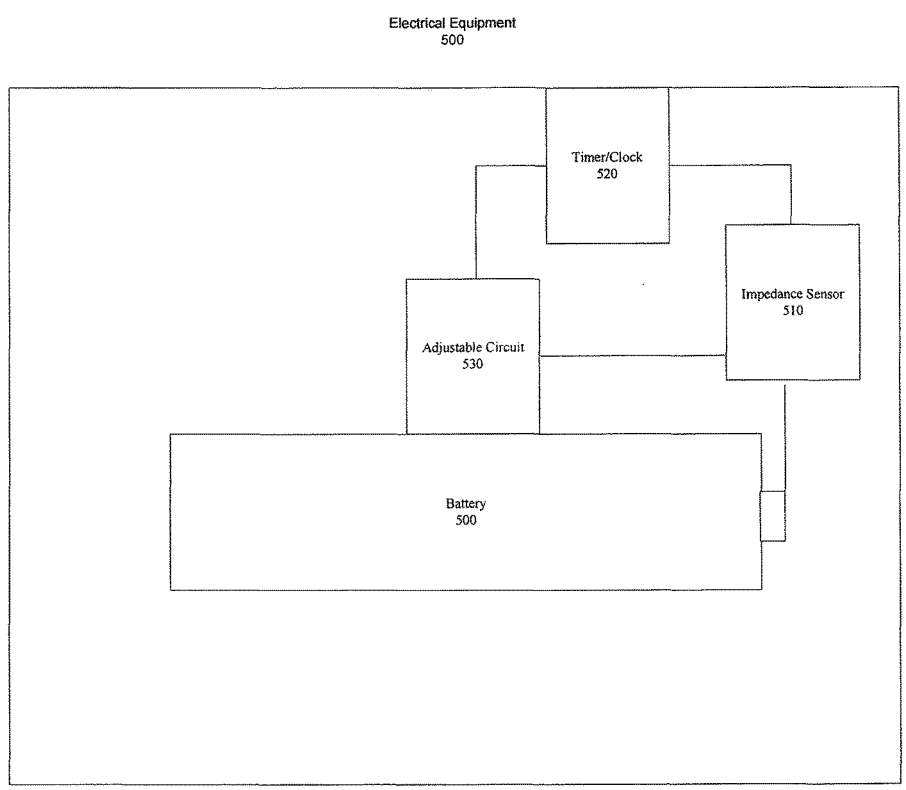
FIG. 5 shows another exemplary piece of adjustable electrical equipment, according to an aspect of the present disclosure.

FIG. 5 shows another exemplary piece of adjustable electrical equipment, according to an aspect of the present disclosure. In FIG. 5, internal impedance of a battery 500 is measured by impedance sensor 510, and an adjustable circuit 530 is adjusted based on measurements of the impedance sensor 510. A timer clock 520 may be set to monitor the duration of a testing and adjustment cycle based on an initial measurement of the impedance sensor 510. In FIG. 5, all of the noted elements are provided as components of a single piece of electrical equipment 500. In other words, no external instructions are required in order to start and end the testing and adjustment described herein, such as when the testing is performed on a preset periodic cycle. Further, the entirety testing and adjustment process described herein can be provided based on a preset time stored in the timer/clock 520, or based on detection of a particular action such as the electrical equipment 500 being turned on or detection of a "test" button on the electrical equipment 500 being pushed.

Figure 6:
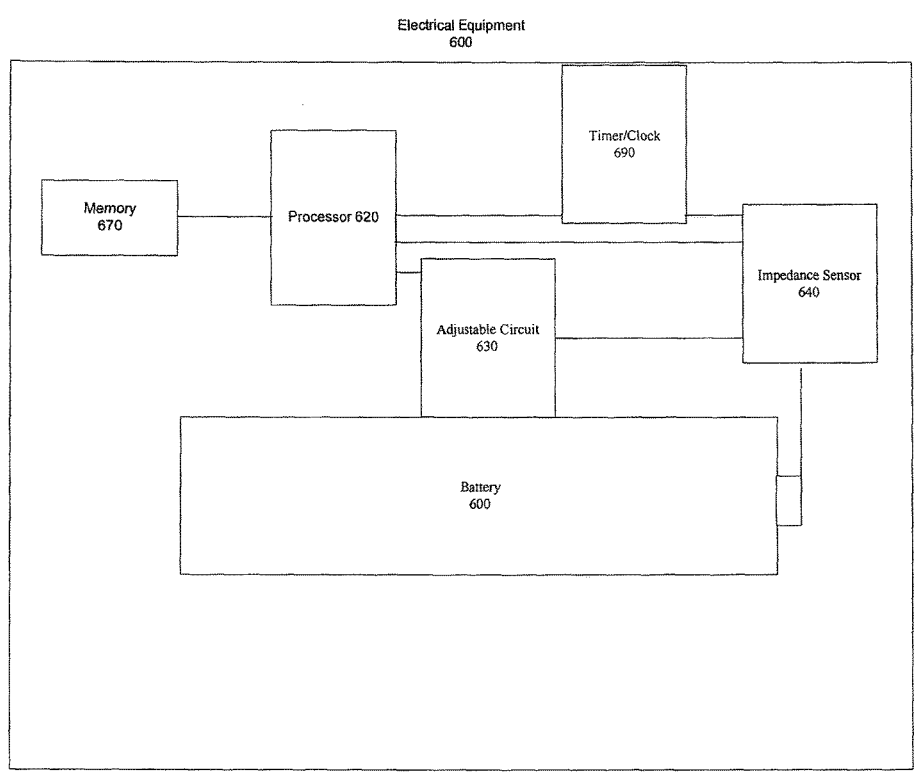
FIG. 6 shows another exemplary piece of adjustable electrical equipment, according to an aspect of the present disclosure.

FIG. 6 shows another exemplary piece of adjustable electrical equipment, according to an aspect of the present disclosure. In FIG. 6, a memory 670 and processor 620 are provided to control the adjustable circuit 630 using instructions stored in the memory 670. A processor 620 as described herein is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. A processor 620 is an article of manufacture and/or a machine component. A processor 620 is configured to execute software instructions in order to perform functions as described herein. A processor 620 may be a general purpose processor or may be part of an application specific integrated circuit (ASIC). A processor 620 may also be a microprocessor, a microcomputer, a processor chip, a controller, a microcontroller, a digital signal processor (DSP), a state machine, or a programmable logic device. A processor 620 may also be a logical circuit, including a programmable gate array (PGA) such as a field programmable gate array (FPGA), or another type of circuit that includes discrete gate and/or transistor logic. A processor 620 may be a central processing unit (CPU). Additionally, any processor described herein may include multiple processors, parallel processors, or both. Multiple processors may be included in, or coupled to, a single device or multiple devices.

A memory 670 described herein is a tangible storage medium that can store data and executable instructions, and is non-transitory during the time instructions are stored therein. A memory 670 described herein is an article of manufacture and/or machine component. A memory 670 described herein is a computer-readable medium from which data and executable instructions can be read by a computer. A memory 670 as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. A memory 670 may be volatile or non-volatile, secure and/or encrypted, unsecure and/or unencrypted.

In FIG. 6, internal impedance of a battery 600 is measured by impedance sensor 640, and an adjustable circuit 630 is adjusted based on measurements of the impedance sensor 640. A timer clock 690 may be set to monitor the duration of a testing and adjustment cycle based on an initial measurement of the impedance sensor 640. In FIG. 6, all of the noted elements are again provided as components of the electrical equipment 600. In other words, no external instructions are required in order to start and end the testing and adjustment described herein, such as when the testing is performed on a preset periodic cycle.

Figure 7:
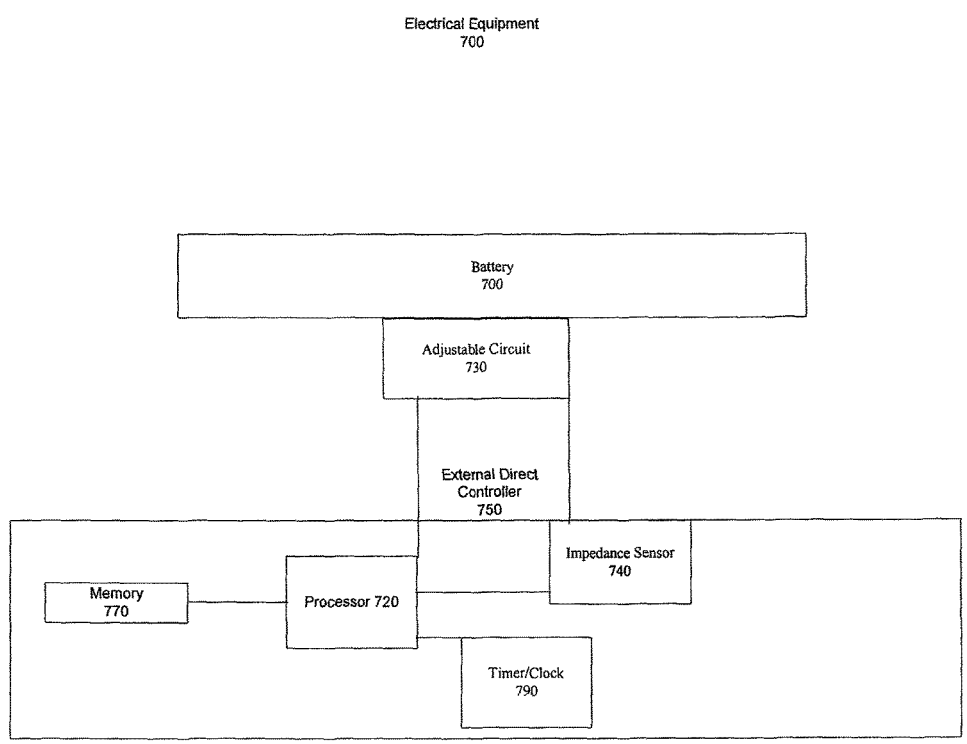
FIG. 7 shows an exemplary system for adjustable electrical equipment, according to an aspect of the present disclosure.

FIG. 7 shows an exemplary system for adjustable electrical equipment, according to an aspect of the present disclosure. In FIG. 7, the battery 700 is connected to an adjustable circuit 730, but is otherwise controlled externally by an external direct controller 750. The external direct controller 750 may be an external adjunct to a piece of electrical equipment that includes the battery 700. In FIG. 7, the external direct controller 750 has an impedance sensor 740 for sensing the internal impedance of the battery 700, a timer clock 790 for recording time and communicating with a processor 720, and the processor 720 and a memory 770 for executing and storing instructions. In FIG. 7, the testing and adjustment using the adjustable circuit 730 are performed at the instruction of the processor 720, whether using preset instructions or dynamic instructions.

Figure 8:
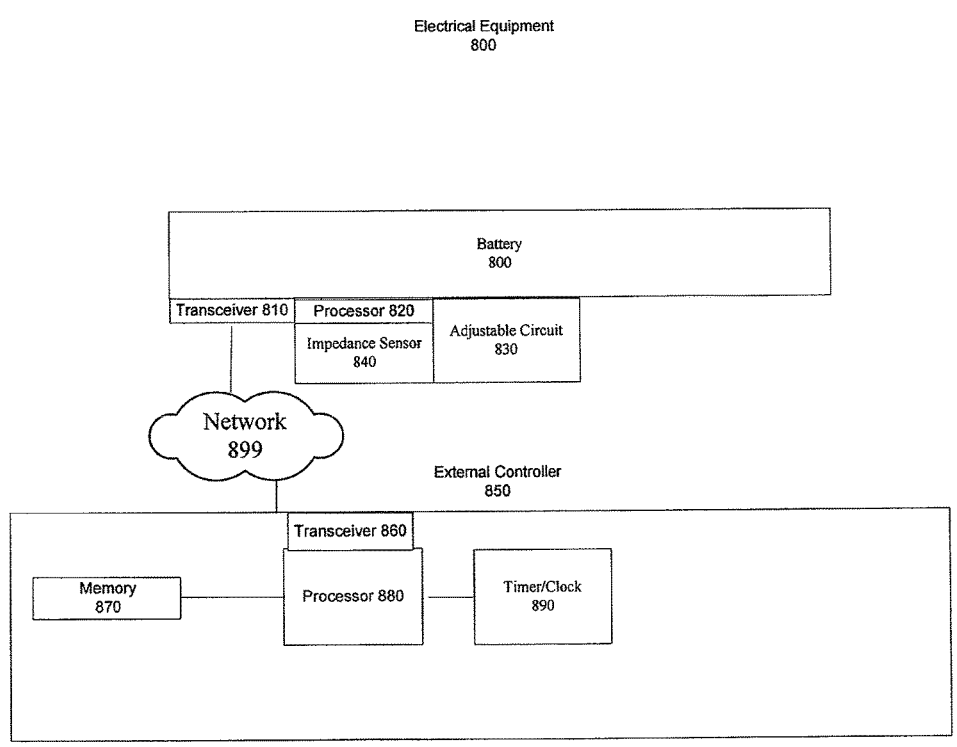
FIG. 8 shows another exemplary system for adjustable electrical equipment, according to an aspect of the present disclosure.

FIG. 8 shows another exemplary system for adjustable electrical equipment, according to an aspect of the present disclosure. In FIG. 8, a battery 800 is in contact with an adjustable circuit 830, and an impedance sensor 840 senses the internal impedance of the battery 800. A transceiver 810 is also provided with the battery 800 to communicate across a network 899 with an external controller 850. In FIG. 8, a processor 820 may receive instructions via the transceiver 810 in order to start the testing with the impedance sensor 840 and the adjustment with the adjustable circuit 830. The external controller 850 in FIG. 8 can also include a transceiver 860, which in turn receives instructions from a processor 880. The external controller 850 may also have a memory 870 to store instructions and data used by the processor 880, and a time/clock for marking and setting time such as periodic start times to start testing and adjustment and duration of time periods during which testing and adjustment can be performed.

As described herein, when a device starts up for a periodic self-test, the current and battery output voltage are measured with two different loads applied in order to assess the apparent internal battery impedance. In the case of, e.g., passivation, the impedance can be reduced by increasing the current draw, effectively "burning off" the impedance cause. The apparent battery impedance is measured and the load current can be dynamically adjusted (increased) until the internal battery impedance drops to an acceptable level. The negative impact of increasing battery impedance can be reduced while also minimizing the impact on battery life.

In the embodiments described herein, measurement of battery impedance is performed by measuring battery voltage twice (at two separate values) and measuring or otherwise identifying battery current twice. The battery impedance may be measured using only resistance when the battery can be isolated in a DC circuit, or may be measured using capacitance and inductance also when the batter is in an AC circuit.

A process described herein can include the unit waking and powering up, measuring battery voltage (V1), measuring battery current or using a nominal reference value for battery current (I1), placing a somewhat higher load on the battery, measuring battery voltage (V2), measuring battery current or using a nominal reference value for battery current (I2), calculating apparent ohmic load of the unit from V=IR for both measurements, resulting in two loads: R1 and R2.

If the open circuit voltage of the battery is Vb, and the internal resistance of the battery is Rb, the open circuit voltage of the battery is calculable from Vb=Ix (Rb+Rx), where "x" is the "1" or "2" from the steps above. The two equations that result (from the two measurements) are: Vb=I1 (Rb+R1) and Vb=I2 (Rb+R2). Setting these two equations to be equal, I1 (Rb+R1) =I2 (Rb+R2). Solving the equation for the internal resistance of the battery, which increases as the battery ages and with passivation or similar effects, the equation becomes Rb=(I1*R1−I2*R2)/(I2−I1).

If the internal resistance of the battery has increased beyond some threshold, Rth, the load current is increased in order to drive off the passivation. The load can be increased incrementally, such as from 0 to a single low level, or from multiple different levels that can be selected using one or more switches, one or more capacitors, and a variable charging time for charging the capacitor(s). As a result, if the internal resistance is caused by passivation or some other degradation that can be mitigated with high current, battery resistance Rb will gradually decrease. Eventually, Rb will drop below a threshold and the testing process can end. The rate in load increase can also be controlled to ensure V2 does not drop below a minimum level. If Rb does not go below the threshold within a set amount of time, the battery may be deemed bad.

Low values may be set as placeholders for the initial measurements. The entire operation can be written as a process that can be executed by a processor as long as the processor can control an adjustable circuit as described herein. A process may be written using software to force the increase in current.

In the manner described herein, testing does not have to be performed with different schedules. Rather, testing may be performed as a self-test using preset/preloaded instructions, or may be controlled externally and even initiated dynamically. The same testing process may be performed multiple consecutive times or even every time, and the testing process can include dynamically adjusting current to burn off the cause of battery impedance such as passivation.

The testing and adjustment described herein may be useful for any type of electrical equipment that is infrequently used. The testing and adjustment described herein may be incorporated into electrical equipment that performs periodic self-tests. The testing and adjustment is notably suitable for lithium primary cells and products that run on lithium primary cells, where the chemistry is likely to exhibit long term degradation due to low current.

Although adjustable electrical equipment has been described with reference to several exemplary embodiments, it is understood that the words that have been used are words of description and illustration, rather than words of limitation. Changes may be made within the purview of the appended claims, as presently stated and as amended, without departing from the scope and spirit of adjustable electrical equipment in its aspects. Although adjustable electrical equipment has been described with reference to particular means, materials and embodiments, adjustable electrical equipment is not intended to be limited to the particulars disclosed; rather adjustable electrical equipment extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

As described above, the apparent battery impedance can be reduced by a feedback process in which the load current applied varies based on the magnitude of the measured apparent battery impedance. This helps maximize battery life compared to automatically using a high load current at each test, such as without using or even measuring the apparent battery impedance. As described herein, the load current may be dynamically adjusted based on the measured apparent battery impedance, and the process may include iteratively measuring the apparent battery impedance and adjusting the load current more than once.

Of course, the process may include measuring apparent battery impedance and setting a load current only once, such as when the load current does not need to be readjusted a second time. In this case, the load current is still set to a selected value as a result of the measurement of the apparent battery impedance.

According to an aspect of the present disclosure, electrical apparatus includes a battery and an adjustable circuit. The adjustable circuit is configured to adjust a load current in the electrical equipment when battery impedance for the battery is higher than a predetermined threshold battery impedance. The battery impedance for the battery is compared in a session against the predetermined threshold battery impedance and the load current is adjusted in the session when the predetermined threshold battery impedance is higher than the predetermined threshold battery impedance.

According to another aspect of the present disclosure, the electrical apparatus includes a sensor that measures the battery impedance for the battery in the session.

According to yet another aspect of the present disclosure, the load current is dynamically adjusted in the electrical equipment in the session when the battery impedance measured is higher than the predetermined threshold battery impedance.

According to still another aspect of the present disclosure, the battery impedance is repeatedly compared and the load current repeatedly adjusted in the session until the battery impedance is lower than the predetermined threshold battery impedance. Comparison of the battery impedance and adjustment of the load current is stopped in the session when the battery impedance is lower than the predetermined threshold battery impedance.

According to another aspect of the present disclosure, the electrical apparatus includes a timer. The battery impedance is repeatedly compared and the load current repeatedly adjusted in the session until the battery impedance is lower than the predetermined threshold battery impedance or a predetermined time expires according to the timer.

According to yet another aspect of the present disclosure, the battery impedance for the battery is compared as part of a self-test performed by the electrical apparatus.

According to still another aspect of the present disclosure, the load current is adjusted in a self-test performed using pre-set instructions.

According to another aspect of the present disclosure, the electrical apparatus includes a memory that stores pre-set instructions to perform a self-test including comparing the battery impedance for the battery against the predetermined threshold battery impedance.

According to yet another aspect of the present disclosure, the battery impedance is compared and the load current adjusted in the session repeatedly and continuously until a predetermined time expires or the battery impedance is lower than the predetermined threshold battery impedance.

According to still another aspect of the present disclosure, the electrical apparatus includes a memory that stores instructions, and a processor that executes the instructions. When executed by the processor, the instructions cause the electrical apparatus to perform operations including: waking up a unit that includes the electrical equipment after a first predetermined time expires; performing the comparing and adjusting in the session after the waking up; putting the unit that includes the electrical equipment back to sleep when the measured battery impedance is lower than the predetermined threshold battery impedance; setting a second predetermined time; again waking up the unit that includes the electrical equipment after the second predetermined time expires, and performing the comparing and adjusting again in another session after the unit is again wakened up.

According to another aspect of the present disclosure, the battery impedance is measured in the session by a process. The process includes measuring a first battery voltage (V1) for the electrical equipment; identifying a first battery current (I1) for the electrical equipment; increasing a load on the battery; measuring a second battery voltage (V2) for the electrical equipment after the load on the battery is increased; identifying a second battery current (I2) for the electrical equipment after the load on the battery is increased; calculating a first battery impedance (R1) for the electrical equipment from V1/I1; calculating a second battery impedance (R2) for the electrical equipment from V2/I2; and calculating a battery internal impedance Rb From I1(Rb+R1)=I2(Rb+R2). The battery internal impedance Rb is the measured battery impedance.

According to yet another aspect of the present disclosure, the identified first battery current is assigned a first predetermined nominal value, and the identified second battery current is assigned a second predetermined nominal value.

According to still another aspect of the present disclosure, the first battery impedance R1 and second battery impedance are apparent ohmic loads of the electrical equipment not including the battery.

According to another aspect of the present disclosure, the battery internal voltage Vb is an open circuit voltage of the battery.

According to yet another aspect of the present disclosure, the process further includes ensuring that the second battery voltage V2 does not drop below a minimum threshold level.

According to still another aspect of the present disclosure, the electrical equipment wakes up for a periodic self-test, identifies battery current and battery voltage with two different loads applied, and calculates battery internal impedance as the measured battery impedance.

According to another aspect of the present disclosure, the battery impedance for the battery is reduced by increasing the load current for the battery in the electrical equipment.

According to yet another aspect of the present disclosure, the electrical apparatus includes a capacitor. The load current is dynamically increased by a process that includes charging the capacitor.

According to still another aspect of the present disclosure, the electrical equipment is medical equipment.

According to another aspect of the present disclosure, the electrical equipment performs a self-test involving measuring the battery impedance, comparing the measured battery impedance against the predetermined threshold battery impedance, and dynamically adjusting the load current. The self-test is performed based on instructions stored on the self-testing electrical equipment and independent of any instructions received over a communication network.

According to yet another aspect of the present disclosure, the battery is a lithium ion battery.

According to an aspect of the present disclosure, a method for performing a test protocol for electrical equipment includes comparing measured battery impedance for a battery of the electrical equipment against a predetermined threshold battery impedance in a session. The method also includes adjusting a load current applied to the battery of the electrical equipment in the session when the measured battery impedance is higher than the predetermined threshold battery impedance.

According to another aspect of the present disclosure, the method includes measuring, by the electrical equipment, the battery impedance for the battery of the electrical equipment in the session.

According to yet another aspect of the present disclosure, the method includes repeating the comparing and adjusting in the session until the measured battery impedance is lower than the predetermined threshold battery impedance, and stopping the comparing and adjusting when the measured battery impedance is lower than the predetermined threshold battery impedance.

According to still another aspect of the present disclosure, the method includes repeating the comparing and adjusting in the session until a predetermined time period expires, and stopping the comparing and adjusting when the predetermined time period expires though the measured battery impedance is higher than the predetermined threshold battery impedance.

According to another aspect of the present disclosure, the method is performed continuously in the session until the measured battery impedance is lower than the predetermined threshold battery impedance or until the predetermined time period expires.

According to yet another aspect of the present disclosure, the adjusting the load current includes increasing the load current until the battery impedance drops to the predetermined threshold battery impedance.

According to still another aspect of the present disclosure, the method is performed as a self-test using pre-loaded instructions. The self-test is performed independent of any instructions received over a network.

According to another aspect of the present disclosure, the method includes waking up a unit that includes the electrical equipment after a first predetermined time expires; performing the comparing and adjusting in the session after the waking up; putting the unit that includes the electrical equipment back to sleep when the measured battery impedance is lower than the predetermined threshold battery impedance; setting a second predetermined time; again waking up the unit that includes the electrical equipment after the second predetermined time expires, and performing the comparing and adjusting again in another session after the unit is again wakened up.

According to yet another aspect of the present disclosure, the measuring the battery impedance includes measuring a first battery voltage (V1) for the electrical equipment; identifying a first battery current (I1) for the electrical equipment; increasing a load on the battery; measuring a second battery voltage (V2) for the electrical equipment after the load on the battery is increased; identifying a second battery current (I2) for the electrical equipment after the load on the battery is increased; calculating a first battery impedance (R1) for the electrical equipment from V1/I1; calculating a second battery impedance (R2) for the electrical equipment from V2/I2; and calculating a battery internal impedance Rb From I1(Rb+R1)=I2(Rb+R2). The battery internal impedance Rb is the measured battery impedance.

According to still another aspect of the present disclosure, the identified first battery current is assigned a first predetermined nominal value. The identified second battery current is assigned a second predetermined nominal value.

According to another aspect of the present disclosure, the electrical equipment wakes up for a periodic self-test, identifies battery current and battery voltage with two different loads applied, and calculates battery internal impedance as the measured battery impedance.

According to another aspect of the present disclosure, the comparing and adjusting are performed periodically together as a self-test by the electrical equipment.

According to an aspect of the present disclosure, a battery circuit includes a battery and an adjustable circuit. The adjustable circuit is configured to apply an adjusted load current to the battery in a continuous process when battery impedance for the battery is measured to be higher than a predetermined threshold battery impedance. The adjustable circuit is also configured to stop applying the adjusted load current to the battery in the continuous process when the battery impedance for the battery is measured to be lower than the predetermined threshold battery impedance after being measured to be higher than a predetermined threshold battery impedance.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to make or use the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical device, comprising:
a battery that is removable from the medical device;
a memory that stores instructions to perform a periodic self-test,
a processor communicatively coupled to the memory and the battery and configured to execute the instructions to perform the periodic self-test, the instructions to perform the periodic self-test including:
power up of the medical device at one or more preset times, and
a duration of the periodic self-test;

an adjustable circuit communicatively coupled to the processor and configured to adjust a load current on the battery during the periodic self-test in response to commands from the processor;

a sensor used to obtain a battery impedance for the battery for the duration of the self-test; and wherein, for the duration of the periodic self-test:

the battery impedance for the battery is repeatedly measured;

each measured battery impedance is compared against a predetermined threshold battery impedance, and the load current on the battery is repeatedly adjusted until the measured battery impedance is lower than the predetermined threshold battery impedance; and wherein the battery impedance is measured by:

calculating a first battery impedance (R1) for the medical device, increasing a load on the battery, calculating a second battery impedance (R2) for the medical device, calculating a battery internal impedance Rb from the first battery impedance and the second battery impedance, and determining battery internal impedance Rb as the measured battery impedance based on the first and second calculated impedances.

2. The medical device of claim 1, wherein the load current is dynamically adjusted in the medical device for the duration of the periodic self-test when the measured battery impedance is higher than the predetermined threshold battery impedance.

3. The medical device of claim 1, further comprising:

a timer, wherein the battery impedance is repeatedly compared and the load current repeatedly adjusted for the duration of the periodic self-test until the battery impedance is lower than the predetermined threshold battery impedance or a predetermined time expires according to the timer.

4. The medical device of claim 1, wherein the battery impedance is compared to the predetermined threshold battery impedance and the load current adjusted repeatedly and continuously for the duration of the periodic self-test until a predetermined time expires or the battery impedance is lower than the predetermined threshold battery impedance.

5. The medical device of claim 1, wherein, when executed by the processor, the instructions cause the medical device to perform operations including:

powering up the medical device after a first predetermined time expires;

performing the comparing and adjusting of the measured battery impedance the predetermined threshold battery impedance after the powering up;

putting the medical device back to sleep when the measured battery impedance is lower than the predetermined threshold battery impedance;

setting a second predetermined time;

again powering up medical device after the second predetermined time expires, and performing the comparing and adjusting of the measured battery impedance and the predetermined threshold battery impedance again after the medical device is again powered up.

6. The medical device of claim 1, wherein the battery impedance is measured during the periodic self-test by a process that includes:

measuring a first battery voltage (V1) for the medical device;

identifying a first battery current (I1) for the medical device;

increasing a load on the battery;

measuring a second battery voltage (V2) for the medical device after the load on the battery is increased;

identifying a second battery current (I2) for the medical device after the load on the battery is increased;

calculating the first battery impedance (R1) for the medical device from V1/I1;

calculating the second battery impedance (R2) for the medical device from V2/I2; and calculating the battery internal impedance Rb From I1(Rb+R1)=I2(Rb +R2), and wherein the battery internal impedance Rb is the measured battery impedance.

7. The medical device of claim 6, wherein the identified first battery current is assigned a first predetermined nominal value, and wherein the identified second battery current is assigned a second predetermined nominal value.

8. The medical device of claim 6, wherein the first battery impedance R1 and second battery impedance comprise apparent ohmic loads of the medical device not including the battery.

9. The medical device of claim 6, wherein a battery internal voltage Vb comprises an open circuit voltage of the battery.

10. The medical device of claim 6, wherein the instructions for the periodic self-test further comprises:

ensuring that the second battery voltage V2 does not drop below a minimum threshold level.

11. The medical device of claim 1, wherein the medical device powers up for the periodic self-test, identifies battery current and battery voltage with two different loads applied, and calculates battery internal impedance as the measured battery impedance.

12. The medical device of claim 1, wherein the battery impedance for the battery is reduced by increasing the load current for the battery in the medical device.

13. The medical device of claim 1, further comprising:

a capacitor, wherein the load current is dynamically increased by a process that includes charging the capacitor.

14. The medical device of claim 1, wherein the medical device comprises a defibrillator.

15. The medical device of claim 1, wherein the self-test is performed based on the instructions stored in the memory of the medical device and independent of any instructions received over a communication network.

16. The medical device of claim 1, wherein the battery comprises a lithium ion battery.

17. A method for performing a periodic self-test for a medical device, comprising:

storing instructions to perform a periodic self-test in a memory of the medical device;

executing the instructions to initiate the periodic self-test by a processor of the medical device, the instructions including:

duration of the self-test, and powering up the medical device at one or more preset times;

identifying a battery current and a battery voltage with at least two different loads applied and calculating a battery impedance as the measured battery impedance;

and wherein, for the duration of the self-test:
repeatedly measuring a battery impedance of a battery,
comparing each measured battery impedance for the battery of the medical device against a predetermined threshold battery impedance and
repeatedly adjusting a load current applied to the battery of the medical device until the measured battery impedance is lower than the predetermined threshold battery impedance; and wherein the battery impedance is measured by:
calculating a first battery impedance (R1) for the medical device,
increasing a load on the battery,
calculating a second battery impedance (R2) for the medical device,
calculating a battery internal impedance Rb from the first battery impedance and the second battery impedance, and
determining battery internal impedance Rb as the measured battery impedance based on the first and second calculated impedances.

18. The method of claim 17, further comprising: stopping the repeated comparing and adjusting when the measured battery impedance is lower than the predetermined threshold battery impedance.

19. The method of claim 17, further comprising:
repeating the comparing and adjusting for the duration of the periodic self-test, and
stopping the comparing and adjusting when at an end of the duration of the periodic self-test even if the measured battery impedance is higher than the predetermined threshold battery impedance.

20. The method of claim 17, wherein the method is performed continuously for the duration of the periodic self-test until the measured battery impedance is lower than the predetermined threshold battery impedance or until an end of the periodic self-test.

21. The method of claim 17, wherein the adjusting the load current comprises increasing the load current until the battery impedance drops to the predetermined threshold battery impedance.

22. The method of claim 17, wherein the self-test is performed independent of any instructions received over a network.

23. The method of claim 17, further comprising:
performing a first powering up of the medical device after a first predetermined time expires;
performing the repeated comparing and adjusting for a first duration of a first periodic self-test after the first powering; powering down the medical device when the measured battery impedance is lower than the predetermined threshold battery impedance;
setting a second predetermined time;
performing a second powering up of the medical device after the second predetermined time expires, and
performing the repeated comparing and adjusting again for a second duration of a second periodic self-test,
wherein the first duration of the first periodic self-test is a different length than the second duration of the second periodic self-test.

24. The method of claim 17,
wherein the measuring the battery impedance comprises:
measuring a first battery voltage (V1) for the medical device;
identifying a first battery current (I1) for the medical device;
increasing a load on the battery;
measuring a second battery voltage (V2) for the medical device after the load on the battery is increased;
identifying a second battery current (I2) for the medical device after the load on the battery is increased;
calculating the first battery impedance (R1) for the medical device from V1/I1;
calculating the second battery impedance (R2) for the medical device from V2/I2; and
calculating the battery internal impedance Rb From I1(Rb+R1)=I2(Rb +R2), and
wherein the battery internal impedance Rb is the measured battery impedance.

25. The method of claim 17, wherein the identified first battery current is assigned a first predetermined nominal value, and wherein the identified second battery current is assigned a second predetermined nominal value.

26. The medical device of claim 1, wherein the medical device includes a defibrillator.

* * * * *